(12) United States Patent
Inoue et al.

(10) Patent No.: US 10,098,725 B2
(45) Date of Patent: *Oct. 16, 2018

(54) ENDOVASCULAR TREATMENT AID

(71) Applicants: Toray Industries, Inc., Tokyo (JP); Kanji Inoue, Kyoto (JP)

(72) Inventors: Kanji Inoue, Kyoto (JP); Takahiro Yagi, Otsu (JP); Masaki Fujita, Otsu (JP); Koji Kadowaki, Otsu (JP); Kazuhiro Tanahashi, Otsu (JP)

(73) Assignees: Toray Industries, Inc. (JP); Kanji Inoue (JP)

( * ) Notice: Subject to any disclaimer, the term of this patent is extended or adjusted under 35 U.S.C. 154(b) by 108 days.

This patent is subject to a terminal disclaimer.

(21) Appl. No.: 15/308,387

(22) PCT Filed: May 8, 2015

(86) PCT No.: PCT/JP2015/063266
§ 371 (c)(1),
(2) Date: Nov. 2, 2016

(87) PCT Pub. No.: WO2015/170733
PCT Pub. Date: Nov. 12, 2015

(65) Prior Publication Data
US 2017/0065397 A1  Mar. 9, 2017

(30) Foreign Application Priority Data

May 9, 2014 (JP) .................................. 2014-097540
Jul. 30, 2014 (JP) .................................. 2014-154889

(51) Int. Cl.
*A61F 2/01* (2006.01)

(52) U.S. Cl.
CPC ................ *A61F 2/013* (2013.01); *A61F 2/01* (2013.01); *A61F 2002/011* (2013.01);
(Continued)

(58) Field of Classification Search
CPC ........ A61F 2/01–2/013; A61L 33/0035; A61L 35/0041
(Continued)

(56) References Cited

U.S. PATENT DOCUMENTS 5,182,317 A * 1/1993 Winters .............. A61L 33/0029
523/112
5,769,816 A * 6/1998 Barbut .................... A61F 2/013
604/93.01
(Continued)

FOREIGN PATENT DOCUMENTS

JP  2003-505216 A  2/2003
JP  2008-35923 A   2/2008
(Continued)

*Primary Examiner* — Kathleen Holwerda
(74) *Attorney, Agent, or Firm* — DLA Piper LLP (US)

(57) ABSTRACT

An endovascular treatment aiding device is an endovascular treatment aiding device including a flexible shaft; a filter fixed to the shaft such that an opening section is formed in the proximal side, wherein a ring having elastic restoring force is fixed to the opening section, which filter is capable of being opened and closed in an umbrella-like manner, and is in a conical shape having a bottom formed by the ring when the filter is open; and a linear supporting member fixed to the ring and a part of the shaft such that they are connected to each other, which linear supporting member enables closing the filter by application of an external force to the proximal side; wherein coils formed with a radio-opaque material is/are wound around the ring; when the filter is closed, a plurality of mountains pointing toward the distal side and a plurality of valleys pointing toward the proximal side are alternately formed in the ring to form a shape in which the mountains are positioned close to each other, and the valleys are positioned close to each other; and the coils are arranged on the ring such that the coils contain the positions fixed by the supporting member on the ring, but
(Continued)

do/does not contain the positions of the peaks of the mountains and the peaks of the valleys.

9 Claims, 4 Drawing Sheets

(52) U.S. Cl.
CPC . *A61F 2002/016* (2013.01); *A61F 2230/0067* (2013.01); *A61F 2250/0098* (2013.01)

(58) Field of Classification Search
USPC .......................................................... 606/200
See application file for complete search history.

(56) References Cited

U.S. PATENT DOCUMENTS

| | | | |
|---|---|---|---|
| 6,530,939 B1 | 3/2003 | Hopkins et al. | |
| 2003/0216807 A1* | 11/2003 | Jones | A61B 17/12022 623/1.22 |
| 2004/0243173 A1* | 12/2004 | Inoue | A61F 2/01 606/200 |
| 2005/0101987 A1 | 5/2005 | Salahieh | |
| 2006/0293705 A1* | 12/2006 | Neilan | A61F 2/013 606/200 |
| 2008/0033483 A1 | 2/2008 | Isshiki et al. | |
| 2008/0097396 A1* | 4/2008 | Spencer | A61M 25/0054 604/525 |
| 2014/0142613 A1 | 5/2014 | Inoue et al. | |
| 2014/0236220 A1 | 8/2014 | Inoue | |
| 2016/0296679 A1 | 10/2016 | Kadowaki et al. | |

FOREIGN PATENT DOCUMENTS

| | | |
|---|---|---|
| JP | 4073869 B2 | 4/2008 |
| JP | 4680201 B2 | 5/2011 |
| WO | 03/084437 A2 | 10/2003 |
| WO | 2008/005898 A2 | 1/2008 |
| WO | 2012176841 A1 | 12/2012 |
| WO | 2013/059069 A2 | 4/2013 |
| WO | 2013047623 A1 | 4/2013 |
| WO | 2015080177 A1 | 6/2015 |

* cited by examiner

ENDOVASCULAR TREATMENT AID

TECHNICAL FIELD

This disclosure belongs to the field of medical instruments, and relates to, in particular, an endovascular treatment aiding device that captures free thrombi or the like during percutaneous treatment for a blood vessel.

JOINT RESEARCH AGREEMENT

This application was made as a result of activities undertaken within the scope of a joint research agreement between Toray Industries, Inc. and Dr. Kanji Inoue.

BACKGROUND

In recent years, the number of patients with cardiac infarction, cerebral infarction or the like is increasing. These infarctions are caused by interruption of blood flow due to obstruction or stenosis of a blood vessel, which occurs by deposition of thrombi, plaques or the like on the vascular wall. In general, for treatment of a site of obstruction or stenosis in a blood vessel, percutaneous treatment by balloon angioplasty or stenting using a balloon catheter or a stent is carried out.

In treatment by balloon angioplasty, an inflatable balloon at the distal end portion of a balloon catheter is expanded at a site of obstruction or stenosis in a blood vessel to secure the intravascular lumen and to thereby maintain the blood flow. However, when a blood vessel is expanded by the balloon, thrombi or plaques deposited on the vascular wall might be unexpectedly released, and such a substance might then be carried away by blood flow to cause obstruction of a peripheral thin blood vessel, resulting in infarction.

In treatment by stenting, a stent composed of a material such as nitinol or cobalt alloy having the shape of an almost cylindrical tube or mesh sleeve is permanently or temporarily introduced to a site of stenosis in a blood vessel to secure the intravascular lumen and to thereby maintain the blood flow. However, similar to balloon angioplasty, when the stent is placed in a blood vessel, thrombi or plaques deposited on the vascular wall might be unexpectedly released, causing infarction.

An endovascular treatment aiding device to be used in combination with a treatment device such as a balloon catheter or a stent has been developed to avoid such a risk. The endovascular treatment aiding device is percutaneously placed in a site which is more peripheral than the lesion where the balloon catheter or the stent is to be placed, and used for capturing thrombi or plaques released from the vascular wall.

As such an endovascular treatment aiding device, one having a structure containing: a shaft with an outer diameter which allows the shaft to pass through the guide wire lumen of a treatment device such as a balloon catheter; and a filter fixed at the distal end portion of the shaft; has been reported. The filter has a mesh-shaped or sheet-shaped membrane composed of a polymer material on which a plurality of openings are formed, and has a shape in which the peripheral vessel side, that is, the distal side, is closed, and the central vessel side, that is, the proximal side, is open (JP 2008-35923 A).

By this, during treatment using a treatment device such as a balloon catheter, thrombi or plaques released and carried away from the vascular wall can be captured by the filter constituting a part of the endovascular treatment aiding device placed in the peripheral side, without blocking the blood flow.

When such an endovascular treatment aiding device is used, the endovascular treatment aiding device, with its filter closed, is contained in a delivery sheath, and delivered to the site where the device is to be placed, which is located more peripheral than the lesion. After delivery, the filter is released by removal of the delivery sheath to the outside of the body. This causes self-expansion of the opening section of the filter, thereby allowing close contact of the opening section to the vascular wall. When the endovascular treatment aiding device is to be retrieved, a retrieval sheath is delivered along the endovascular treatment aiding device, and the filter containing thrombi or plaques is stored inside the retrieval sheath, followed by its removal to the outside of the body.

As an endovascular treatment aiding device that enables reduction of leakage of thrombi, plaques or the like by increasing adhesion to the vascular wall, an endovascular treatment aiding device comprising a ring-shaped member formed with a superelastic metal provided in the opening section of the filter, wherein, when the opening section of the filter is closed by bundling of the support member supporting the filter, the superelastic metal is transformed to allow folding of the filter into a bag shape, has been reported (JP 4073869 B).

An endovascular treatment aiding device comprising a coil made of a radio-opaque material arranged on a ring-shaped filter opening section, which enables observation under radiation, has been reported for the purpose of easily allowing observation of whether the filter is in close contact with the vascular wall during the operation, and whether the opening section of the filter was securely closed upon retrieval of the device (JP 4680201 B).

When such an endovascular treatment aiding device is placed in a blood vessel, the living body recognizes it as a foreign substance, and blood coagulation reaction proceeds to cause formation of a thrombus. Therefore, antithrombogenicity is required for the device. In view of this, endovascular treatment aiding devices to which antithrombogenic compounds are given have been reported (WO 2003/084437, WO 2008/005898 and WO 2013/059069).

However, in the endovascular treatment aiding device described in JP 2008-35923 A, contact with the stent may occur during delivery of a retrieval sheath because of the thick diameter of the distal end of the retrieval sheath so that there is a possibility that the retrieval sheath cannot be delivered to the filter. Moreover, since the opening section of the filter does not have a ring shape, its adhesion to the vascular wall is insufficient so that there is a possibility of leakage of thrombi, plaques or the like during treatment using a balloon catheter or the like.

In the endovascular treatment aiding device described in JP 4073869 B, the superelastic metal used for the ring-shaped filter opening section lacks radio-opaque properties so that observation by radiation transmission during the ordinary operation is impossible. Thus, there is a possibility that whether or not the device is securely adhering to the vascular wall, or whether or not the opening section of the filter has been securely closed upon retrieval of the device, cannot be known.

In the endovascular treatment aiding device described in JP 4680201 B, the superelasticity of the ring-shaped filter opening section is lost in the place where the coil formed with a radio-opaque material is arranged. Thus, the ring-shaped filter opening section cannot be appropriately transformed. Hence its secure adhesion to the vascular wall is impossible so that there is a possibility of leakage of thrombi, plaques or the like. Although the document also describes partial arrangement of the coil formed with a radio-opaque material, there is no description on a specific arrangement with which the decrease in the adhesion to the vascular wall can be prevented.

Although WO 2003/084437, WO 2008/005898 and WO 2013/059069 describe giving of antithrombogenic compounds to endovascular treatment aiding devices, there is no description on the optimal types and combinations of the antithrombogenic compounds.

That is, conventionally, there is no known endovascular treatment aiding device that solves both of the two problems, that is, there is no known endovascular treatment aiding device that allows confirmation of its secure adhesion to a blood vessel, and also allows prevention of leakage of a substance such as thrombi or plaques captured.

It could therefore be helpful to provide an endovascular treatment aiding device that allows confirmation of its secure adhesion to a blood vessel, and also allows prevention of leakage of substances such as plaques captured.

SUMMARY

We thus provide (1) to (10):

(1) An endovascular treatment aiding device comprising:
a flexible shaft;
a filter fixed to the shaft such that a closed-end section is formed in the distal side in the longitudinal direction of the shaft, and an opening section is formed in the proximal side in the longitudinal direction, wherein a ring having elastic restoring force is fixed to the opening section, which filter is in a conical shape having a bottom formed by the ring when the filter is open, and can be opened and closed in an umbrella-like manner; and
a supporting member composed of linear members each of which is fixed to the ring and a part of the shaft such that these are connected to each other, which linear members enable to close the filter by tension caused by application of an external force to the proximal side in the longitudinal direction;
wherein
coils formed with a radio-opaque material are wound around the ring;
when the filter is closed, a plurality of mountains pointing toward the distal side in the longitudinal direction and a plurality of valleys pointing toward the proximal side in the longitudinal direction are alternately formed in the ring to form a shape in which the mountains are positioned close to each other, and the valleys are positioned close to each other; and
the coils are arranged on the ring such that the coils contain the positions fixed by the supporting member on the ring, but do/does not contain the positions of the peaks of the mountains and the peaks of the valleys.

(2) The endovascular treatment aiding device according to (1), wherein the opening section of the filter and the ring are fixed to each other through an elastomer material.

(3) The endovascular treatment aiding device according to (1) or (2), wherein the coils and the ring are fixed to each other through an elastomer material.

(4) The endovascular treatment aiding device according to any one of (1) to (3), wherein a cationic polymer containing as constituent monomers at least one compound selected from the group consisting of alkyleneimine, vinylamine, allylamine, lysine, protamine, and diallyldimethylammonium chloride is covalently bound to the filter, and an anionic sulfur compound having anticoagulant activity is bound to the filter and/or the cationic polymer.

(5) The endovascular treatment aiding device according to any one of (1) to (4), wherein the ratio of the abundance of nitrogen atoms to the abundance of total atoms on the surface of the filter as measured by X-ray photoelectron spectroscopy (XPS) is 7.0 to 12.0 atomic percent.

(6) The endovascular treatment aiding device according to any one of (1) to (5), wherein the ratio of the abundance of sulfur atoms to the abundance of total atoms on the surface of the filter as measured by X-ray photoelectron spectroscopy (XPS) is 3.0 to 6.0 atomic percent.

(7) The endovascular treatment aiding device according to any one of (1) to (6), wherein the anionic sulfur compound having anticoagulant activity is at least one selected from the group consisting of heparin and heparin derivatives.

(8) The endovascular treatment aiding device according to any one of (1) to (7), wherein the surface amount of the anionic sulfur compound having anticoagulant activity on the filter after soaking in physiological saline at 37° C. for 30 minutes as measured based on the anti-factor Xa activity is not less than 30 mIU/cm$^2$.

(9) The endovascular treatment aiding device according to any one of (1) to (8), wherein the cationic polymer and the anionic sulfur compound having anticoagulant activity form an antithrombogenic compound layer with a thickness of 1 to 600 nm on the surface of the filter.

(10) The endovascular treatment aiding device according to any one of (1) to (9), wherein the filter is formed with polyester.

By identifying the position(s) of the coils formed with the radio-opaque material wound around the ring, secure adhesion of the endovascular treatment aiding device to a blood vessel can be confirmed, and an endovascular treatment aiding device which prevents leakage of substances such as plaques captured can be provided.

DESCRIPTION OF SYMBOLS

Figure 1:
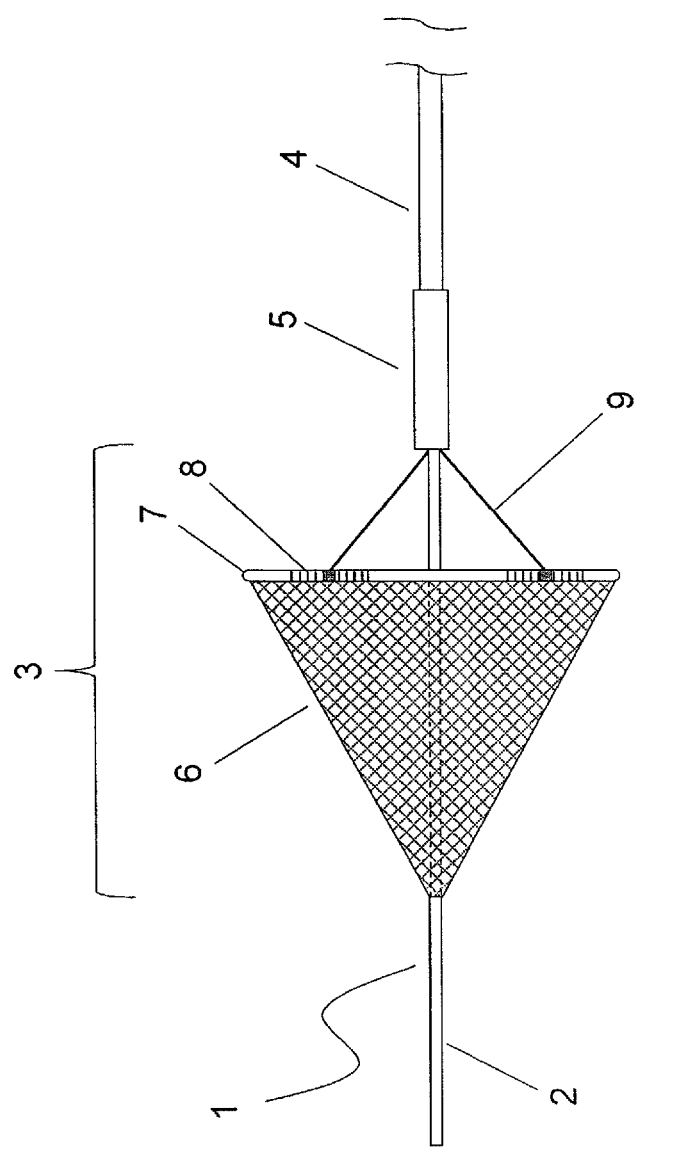
FIG. 1 is a schematic view showing a side view, in the longitudinal direction, of the endovascular treatment aiding device according to an example.

1. Endovascular treatment aiding device
2. Shaft
3. Filter section
4. Outer tube
5. Annular member
6. Filter
7. Ring
8. Coil
9. Supporting member
10. Division point 11. Tube
12. Gauze
13. Particles

DETAILED DESCRIPTION

The endovascular treatment aiding device is characterized in that it comprises:
a flexible shaft;
a filter fixed to the shaft such that a closed-end section is formed in the distal side in the longitudinal direction of the shaft, and an opening section is formed in the proximal side in the longitudinal direction, wherein a ring having elastic restoring force is fixed to the opening section, which filter is in a conical shape having a bottom formed by the ring when the filter is open, and can be opened and closed in an umbrella-like manner; and
a supporting member composed of linear members each of which is fixed to the ring and a part of the shaft such that these are connected to each other, which linear members enable to close the filter by tension caused by application of an external force to the proximal side in the longitudinal direction;
wherein
coils formed with a radio-opaque material are wound around the ring;
when the filter is closed, a plurality of mountains pointing toward the distal side in the longitudinal direction and a plurality of valleys pointing toward the proximal side in the longitudinal direction are alternately formed in the ring to form a shape in which the mountains are positioned close to each other, and the valleys are positioned close to each other;
the coils are arranged on the ring such that the coils contain the positions fixed by the supporting member on the ring, but do/does not contain the positions of the peaks of the mountains and the peaks of the valleys;
a cationic polymer containing, as constituent monomers, a compound selected from the group consisting of alkyleneimine, vinylamine, allylamine, lysine, protamine, and diallyldimethylammonium chloride, is covalently bound to the filter; and
an anionic sulfur compound having anticoagulant activity is bound to the filter and/or the cationic polymer.

Specific examples are described below with reference to drawings. However, this disclosure is not limited to the examples. Each identical element is represented using an identical symbol, and redundant explanations are omitted. The ratios used in the drawings are not necessarily the same as those in the description. The following terms used in the present description are defined as described below unless otherwise specified.

FIG. 1 is a schematic view showing a side view, in the longitudinal direction, of the endovascular treatment aiding device 1 according to an example. The endovascular treatment aiding device 1 shown in FIG. 1 can pass through the inside of a guide wire lumen of a treatment device such as a balloon catheter, and comprises: a linear shaft 2 having flexibility; a filter section 3 which can capture thrombi, plaques or the like; an outer tube 4; and an annular member 5 arranged in the distal side in the longitudinal direction relative to the outer tube 4.

The shaft 2 preferably has flexibility to achieve secure delivery to the peripheral side relative to the lesion where the treatment device is to be placed. The term "having flexibility" herein means that the original shape of the shaft can be recovered after bending the shaft at an angle of 180° such that the radius of curvature is 100D, wherein D represents the diameter of the shaft.

The filter section 3 comprises: a filter 6 in which a plurality of openings are formed, which filter 6 is arranged in the distal side in the longitudinal direction of the shaft 2 and can be opened and closed in an umbrella-like manner; a ring 7 having a circular shape provided in the proximal side in the longitudinal direction of the filter 6, that is, the opening-section side of the filter 6, which ring 7 is composed of a flexible wire having elastic restoring force; coils 8 wound around the ring 7 and formed with a radio-opaque material; and a supporting member 9 composed of linear members arranged between the shaft 2, and the filter 6 and the ring 7, which linear members enable to close the filter 6 by tension caused by application of an external force to the proximal side in the longitudinal direction. The distance between the distal side in the longitudinal direction of the filter 6 and the distal side of the shaft 2 is preferably 5 to 20 mm, more preferably 10 to 15 mm. The distance between the distal side in the longitudinal direction of the balloon portion of the balloon catheter and the proximal side in the longitudinal direction of the filter 6 is preferably not more than 10 mm.

The distal side in the longitudinal direction means the peripheral side of the blood vessel, and the proximal side in the longitudinal direction means the central side of the blood vessel.

The outer tube 4, in which a penetrating hole is formed, is movably arranged on the shaft 2. It can therefore slide on the shaft 2. To improve the kink resistance of the shaft 2, and secure rigidity required to close the filter section 3, a braided layer using a metal wire such as a stainless steel wire or using a resin such as a polyamide may be incorporated in the outer tube 4. The position where the outer tube 4 is fixed on the shaft 2 is also not limited. The position is preferably in the proximal side in the longitudinal direction relative to the opening section of the filter section 3.

The annular member 5, in which a penetrating hole is formed, is movably arranged on the shaft 2. It can therefore slide on the shaft 2. The position where the annular member 5 is fixed on the shaft 2 is also not limited. The position is preferably in the proximal side in the longitudinal direction relative to the opening section of the filter section 3. The position is preferably in the distal side in the longitudinal direction relative to the outer tube 4. The proximal end portion in the longitudinal direction of the annular member 5 may be either fixed or not fixed to the distal end portion in the longitudinal direction of the outer tube 4. During operation, to adjust the position of placement of the endovascular treatment aiding device 1 in the blood vessel, the outer tube 4 in the operator side, where the operator manipulates the device, may be slid toward the distal side or the proximal side in the longitudinal direction. Thus, the proximal end portion in the longitudinal direction of the annular member 5 is preferably fixed to the distal end portion in the longitudinal direction of the outer tube 4 since, without the fixation, the annular member 5 may not follow the sliding of the outer tube 4, and therefore adjustment of the relative positions of the annular member 5 and the filter section 3 may be impossible.

The filter 6 is fixed to the shaft 2 such that the distal side in the longitudinal direction of the filter 6 is closed. This portion of fixation is provided as the closed-end section. The proximal side in the longitudinal direction of the filter 6 is open. This portion is provided as the opening section. To increase adhesion to the vascular wall, the opening section of the filter 6 is fixed to the entire circumference of the ring 7 having a circular shape using an elastomer material. The filter 6 has a conical shape having a bottom formed by the ring 7 when the filter 6 is open. The filter 6 can be opened and closed in an umbrella-like manner such that it follows movement of the ring 7.

Since the coils 8 are fixed to the ring 7 using an elastomer material, flexibility of the ring 7 can be maintained while shifting of the position of the coils 8 due to transformation of the filter 6 and the ring 7 can be prevented.

The supporting member 9 is constituted of a plurality of linear members. In the end portion of the opening-section side of the filter 6, each linear member is fixed to the filter 6, the ring 7, and the coil 8. On the shaft 2, the linear members are fixed together to the same position. By this, the filter 6, the ring 7, and the coils 8 are connected to the part of the shaft 2. In the example shown in FIG. 1, the supporting member 9 is constituted of a plurality of linear members. The number of the linear members is not limited as long as the filter 6 and the ring 7 can be closed. The position where the supporting member 9 is fixed on the shaft 2 is not limited. The position is preferably in the proximal side in the longitudinal direction relative to the opening section of the filter section 3.

Figure 2:
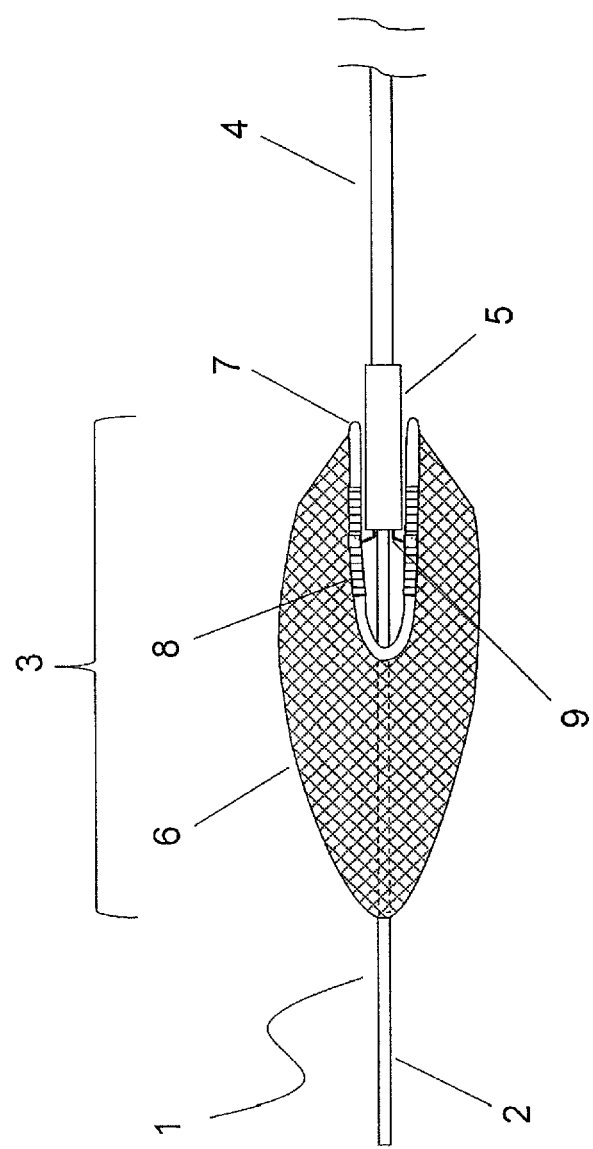
FIG. 2 is a schematic view showing a side view, in the longitudinal direction, of the endovascular treatment aiding device according to an example, wherein the opening section of the filter is closed.

FIG. 2 is a schematic view showing a side view, in the longitudinal direction, of the endovascular treatment aiding device 1 according to an example, wherein the opening section 3 is closed. The penetrating holes formed in the outer tube 4 and the annular member 5 have inner diameters which allow the linear supporting member 9 to pass therethrough. Therefore, when an external force is applied to the proximal side in the longitudinal direction of the supporting member 9 to cause tension, the supporting member 9 is drawn, while being bundled, into the gap between each penetrating hole and the shaft 2, as the supporting member 9 slides on the shaft 2. When the distal end portion in the longitudinal direction of the annular member 5 reaches the position where the drawing of the supporting member 9 has proceeded to the end portion in the opening-section side of the filter section 3, that is, when the annular member 5 finishes bundling of the supporting member 9, the opening section of the filter section 3 becomes a closed state. By making the supporting member 9 have a uniform length, the shaft 2 is in a state where it is positioned on the central axis of the ring 7.

Figure 3:
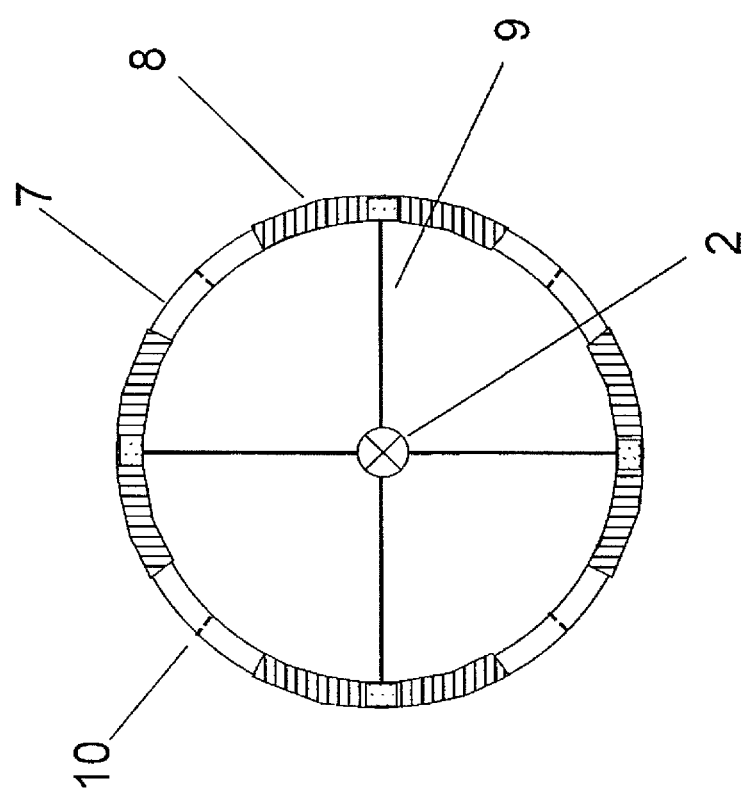
FIG. 3 is a schematic view showing a front view, in the longitudinal direction, of the endovascular treatment aiding device according to an example, wherein the positional relationships among the ring, the coils and the supporting member in the filter section, and the shaft, are illustrated.

FIG. 3 is a schematic view showing a front view, in the longitudinal direction, of the endovascular treatment aiding device 1 according to an example, wherein the positional relationships among the ring 7, the coils 8, and the supporting member 9 in the filter section 3, and the shaft 2, are illustrated. To compactly fold the ring 7 when the opening section of the filter section 3 is closed, not less than four division points are provided on the circumference of the ring 7 such that the circumference is equally divided into an even number of segments, and the supporting member 9 is fixed at all midpoints or alternate midpoints between the neighboring division points. By this, the ring 7 can be bent along the shaft 2 into a wavy shape such that alternate division points form the peaks of the mountains pointing toward the distal side in the longitudinal direction of the shaft 2, and the alternate division points neighboring those division points forming the peaks of the mountains form the peaks of the valleys pointing toward the proximal side in the longitudinal direction of the shaft 2. That is, when the opening section of the filter section 3 is closed, the ring 7 has a shape in which a plurality of mountains pointing toward the distal side in the longitudinal direction of the shaft 2 and a plurality of valleys pointing toward the proximal side in the longitudinal direction are alternately formed, wherein the mountains are positioned close to each other, and the valleys are positioned close to each other. Preferably, as shown in FIG. 3, four division points 10 are provided such that the circumference of the ring 7 is equally divided into four segments, and the supporting member 9 is fixed at the midpoints between the neighboring division points 10. Each midpoint does not need to be positioned exactly in the middle of division points, and may show some deviation toward either one of the division points (with a deviation of not more than ±5° in terms of the central angle formed by two neighboring supporting members and the shaft).

The coils 8 are arranged at positions on the ring 7 including the positions of fixation by the supporting member 9, but not including the peaks of the mountains and the peaks of the valleys. Therefore, the transformation of the ring 7 is not inhibited by the coils 8 so that distortion of the ring 7 during its folding can be prevented. As shown in FIG. 3, when the opening section of the filter section 3 is closed, the filter section 3 has a symmetrical structure and a compactly folded shape as seen from the front in the longitudinal direction. Thus, it is preferred to fix the ring 7 and the coils 8 to the supporting member 9 at the midpoints of the four coils 8 fixed to the ring 7. It is preferred to allow the wire constituting the ring 7 to penetrate the coils 8, to make the structure more stable.

The material of the shaft 2, which acts as the core member of the endovascular treatment aiding device 1, is preferably a metal commonly used for guide wires such as a stainless steel, tungsten, or cobalt alloy.

The material of the outer tube 4 is not limited as long as it can achieve both the rigidity required to close the filter section 3 by tension caused by bundling of the supporting member 9 by the annular member 5, and the flexibility required to secure blood vessel tracking ability. Examples of the material of the outer tube 4 include metals such as nickel alloys and stainless steels. The material of the outer tube 4 is more preferably a resin such as a polyimide or polyamide. When the material of the outer tube 4 is a resin such as a polyimide or polyamide, an easily slidable resin such as a polyimide, polyamide, or polyethylene blended with a polytetrafluoroethylene, tetrafluoroethylene copolymer, and/or lubricant may be incorporated into an inner layer for increasing the slidability of the outer tube 4 on the shaft 2. To secure rigidity required to close the filter section 3, a braided layer prepared using a metal wire such as a stainless steel wire or using a resin such as a polyamide may also be incorporated.

The outer tube 4 may also have a function as a sheath. When the outer diameter of the outer tube 4 is one with which the whole outer tube 4 can be contained in a treatment device such as a balloon catheter, and the inner diameter of the penetrating hole is one with which the whole filter section 3 with its opening section closed can be contained in the penetrating hole, the endovascular treatment aiding device 1 can have a constitution that does not require a sheath.

Examples of the material of the annular member 5 include metals such as stainless steels, platinum alloys, and palladium alloys. To reduce the possibility of damaging the supporting member 9 upon closing of the opening section of the filter section 3, the material of the annular member 5 is more preferably a resin such as a polyimide, polyamide, or polyurethane. From the viewpoint of simplicity in production, the material of the annular member 5 is more preferably a resin such as a polycarbonate, polypropylene, or polyethylene that can be molded using a mold or the like.

Examples of the material constituting the filter 6 include polymers such as polyester, polyurethane, polyether urethane, polyamide, polyvinyl chloride, polycarbonate, polystyrene, polyethylene, polypropylene, polymethylpentene, polymethyl methacrylate, and polytetrafluoroethylene; and superelastic metals such as nickel alloys. The filter 6 is especially preferably constituted using polyester. In terms of the shape of the filter 6, the filter can be provided by preparing a polymer sheet, and forming a plurality of openings thereon. To increase the opening ratio of the filter to secure a sufficient blood passing rate, the filter 6 is more preferably prepared as a mesh using a polymer or a metal processed into a fiber. Examples of the polyester include polyethylene terephthalate (hereinafter referred to as "PET"), polytrimethylene terephthalate, polybutylene terephthalate, polyethylene naphthalate, and polybutylene naphthalate. Among these, PET is more preferred as the base material of the antithrombogenic material because of its versatility.

The pore size is not limited as long as capturing of thrombi or plaques is possible while the blood flow can be secured. When the filter 6 is formed as a sheet, the pore size is preferably 30 to 100 μm. When the filter 6 is formed as a mesh, each opening is preferably 30 to 100 μm on a side. Since the pore size is small, not only capturing of thrombi or plaques released from the vascular wall, but also formation of thrombi due to the filter 6, which is a foreign substance in the human body, may occur. Therefore, an antithrombogenic compound is preferably bound to the surface of the filter 6.

The material of the ring 7 is not limited as long as it is a flexible wire having elastic restoring force that allows free bending of the ring 7. The material is preferably a superelastic metal whose shape can be changed into various shapes, but can be restored to the original ring shape. The ring 7 can therefore be constituted of a shape-memory polymer. The ring 7 is more preferably constituted of a metal such as a nickel alloy.

Possible examples of the elastomer material for fixing the ring 7 and the filter 6 to each other include urethane acrylate adhesives, and polyurethane and polyamide elastomers. From the viewpoint of maintaining the flexibility of the ring 7, the Shore hardness (Shore D) of the material according to ISO868:2003 is preferably about 25 to 55 D. The Shore hardness (Shore A) is more preferably not more than 80 A.

The material of the coil 8 is not limited as long as it is formed with a radio-opaque material. Examples of the material include gold, platinum alloys, and palladium alloys. In terms of the shape of the metal wire used for the coil 8, the metal wire may be a flat rectangular wire or a round wire. The wire diameter of the metal wire to be used as the radio-opaque material is preferably 30 to 70 μm. To reduce the volume of the filter section 3 when its opening section is closed, the wire diameter is more preferably 30 to 40 μm. When the amount of the coils 8 fixed on the ring 7 is too small, the favorable imaging ability of interest can be hardly obtained, while when the amount of the coils 8 fixed on the ring 7 is too large, the transformation of the ring 7 is inhibited. Thus, the total length of the coils 8 with respect to the circumference of the ring 7 is preferably 1/6 to 4/6, more preferably 2/6.

Possible examples of the elastomer material to fix the coil 8 and the ring 7 to each other include urethane acrylate adhesives, and polyurethane and polyamide elastomers. From the viewpoint of maintaining the flexibility of the ring 7, the Shore hardness (Shore D) of the material according to ISO868:2003 is preferably about 20 to 40 D. The Shore hardness (Shore A) is more preferably not more than 90 A. The Shore hardness (Shore A) is still more preferably not more than 80 A.

The material of the supporting member 9 is not limited as long as the restoring force of the ring 7 is not inhibited, and the supporting member 9 is not broken by the bundling into the annular member 5. Examples of the material of the supporting member 9 include thin metal wires. The material of the supporting member 9 is more preferably a high-strength resin fiber such as an aramid fiber, polyarylate fiber, or polyester fiber.

In the filter section 3 of the example, the filter 6 and the supporting member 9 are fixed to each other through the ring 7. Alternatively, the supporting member 9 may be fixed directly, not through the ring 7, to the filter 6. In such a case, the supporting member 9 is preferably formed with a superelastic metal such as a nickel alloy.

The endovascular treatment aiding device is preferably one that suppresses thrombus formation caused thereby, and exerts high antithrombogenicity continuously for a long period. The antithrombogenicity means a property with which blood coagulation does not occur on the surface in contact with blood. For example, the antithrombogenicity means a property that inhibits blood coagulation which proceeds due to platelet aggregation, activation of blood coagulation factors represented by thrombin and/or the like.

The antithrombogenic compound means a compound having antithrombogenicity. In particular, an antithrombogenic compound needs to be bound to the surface of the filter 6, which has a large contacting area with blood and is prone to formation of thrombi.

Specific examples of the antithrombogenic compound include cationic polymers containing, as constituent monomers A, at least one compound selected from the group consisting of alkyleneimine, vinylamine, allylamine, lysine, protamine, and diallyldimethylammonium chloride; and anionic sulfur compounds having anticoagulant activity.

The endovascular treatment aiding device is in a state where antithrombogenicity is given by covalent bonding of a cationic polymer to the surface of the filter 6, and binding of an anionic sulfur compound having anticoagulant activity to the filter 6 and/or the cationic polymer.

Since the constituent monomer A, which is a monomer constituting the cationic polymer, has a cationic nitrogen atom, the polymer is cationic. On the other hand, the compound having anticoagulant activity and containing a sulfur atom is anionic. Therefore, the polymer and the compound can be ionically bound to each other. Examples of the anionic sulfur compound having anticoagulant activity include heparin and heparin derivatives, dextran sulfate, polyvinyl sulfonate, and polystyrene sulfonate. Heparin and heparin derivatives are more preferred. The heparin and heparin derivatives may be either purified or unpurified, and are not limited as long as they can inhibit blood coagulation reaction. Examples of the heparin and heparin derivatives include heparins which are clinically generally and widely used, unfractionated heparins, and low-molecular-weight heparins, as well as heparins having high affinity to antithrombin III. Specific examples of the heparin include "heparin sodium" (manufactured by Organon API Inc.). Examples of the heparin derivatives include Fragmin, Crexane, Orgaran, and Arixtra.

Since cationic polymers have cationic properties, they may exhibit hemolytic toxicity and/or the like so that their elution into blood is not preferred. The cationic polymer is therefore preferably covalently bound to the surface of the filter 6. The covalent bonding of the cationic polymer to the surface of the filter 7 can be carried out by covalently binding a functional group of the cationic polymer to a functional group on the surface of the filter 6 by a well-known method. For example, the covalent bonding can be carried out by binding an amino group of the cationic polymer to a carboxyl group of a polyester constituting the filter 7, using a condensing agent such as 4-(4,6-dimethoxy-1,3,5-triazin-2-yl)-4-methylmorpholinium chloride n-hydrate ("DMT-MM"). As an alternative method, a method in which the cationic polymer is brought into contact with the filter 7 under heat to allow covalent bonding by amino lysis reaction may be used. Alternatively, radiation irradiation may be carried out to cause generation of radicals on the surface of the filter 7 and the cationic polymer, and covalent bonding between the surface of the filter 7 and the polymer may be achieved by recombination reaction of the radicals.

The covalent bond herein means a chemical bond formed by sharing of an electron(s) between atoms. The covalent bond is a covalent bond between atoms such as a carbon atom(s), nitrogen atom(s), oxygen atom(s), and/or sulfur atom(s) present in the cationic polymer and on the surface of the filter 6. The covalent bond may be either a single bond or a multiple bond. Examples of the type of the covalent bond include, but are not limited to, an amine bond, azide bond, amide bond and imine bond. Among these, from the viewpoint of ease of formation of the covalent bond, stability after bonding and the like, an amide bond is more preferred. As a result of intensive study, we discovered that, when amide bonds are formed between the cationic polymer and the surface of the filter 6, the configuration of the cationic polymer on the surface of the filter 6 controls the state of ionic bonding to the anionic sulfur compound having anticoagulant activity. Confirmation of the covalent bonds is possible by observation of the fact that elution does not occur by washing with a solvent that dissolves the polymer.

The cationic polymer may be either a homopolymer or a copolymer. When the cationic polymer is a copolymer, the copolymer may be any of a random copolymer, block copolymer, graft copolymer and alternating copolymer. The cationic polymer is more preferably a block copolymer since, when the block copolymer has a block containing consecutive repeat units containing nitrogen atoms, the block portion interacts with the anionic sulfur compound having anticoagulant activity, to form strong ionic bonds.

The homopolymer means a macromolecular compound obtained by polymerization of a single kind of constituent monomers. The copolymer herein means a macromolecular compound obtained by copolymerization of two or more kinds of monomers. The block copolymer means a copolymer having a molecular structure in which at least two kinds of polymers having different repeat units are covalently bound to each other to form a longer chain. The block means each of the at least two kinds of polymers having different repeat units constituting the block copolymer.

The structure of the cationic polymer may be either linear or branched. The polymer is preferably branched since a branched polymer can form more stable ionic bonds at multiple positions with the anionic sulfur compound having anticoagulant activity.

The cationic polymer has at least one functional group selected from primary to tertiary amino groups and a quaternary ammonium group. In particular, the cationic polymer more preferably has a quaternary ammonium group rather than primary to tertiary amino groups since a quaternary ammonium group has stronger ionic interaction with the anionic sulfur compound having anticoagulant activity and, hence, allows easier control of the elution rate of the anionic sulfur compound having anticoagulant activity.

The carbon numbers of the three alkyl groups constituting the quaternary ammonium group are not limited. However, when the carbon numbers are too large, hydrophobicity is high, and steric hindrance is enhanced so that the anionic sulfur compound having anticoagulant activity cannot effectively bind to the quaternary ammonium group by ionic bonding. When the carbon number is too large, the polymer is more likely to show hemolytic toxicity so that the carbon number per alkyl group bound to the nitrogen atom constituting the quaternary ammonium group is preferably 1 to 12, more preferably 2 to 6. The carbon numbers of the three alkyl groups bound to the nitrogen atom constituting the quaternary ammonium group may be the same as or different from each other.

A polyalkyleneimine is preferably used as the cationic polymer since the amount of the anionic sulfur compound having anticoagulant activity adsorbed thereto by ionic interaction can be large. Examples of the polyalkyleneimine include polyethyleneimines (hereinafter referred to as "PEIs"), polypropyleneimines, and polybutyleneimines, as well as alkoxylated polyalkyleneimines. Among these, PEIs are more preferred.

Specific examples of the PEIs include "LUPASOL" (registered trademark) (manufactured by BASF) and "EPOMIN" (registered trademark) (manufactured by Nippon Shokubai Co., Ltd.). The PEI may be a copolymer with other monomers, or may be a modified body, as long as the desired effect is not deteriorated. The modified body herein means a cationic polymer which has the same monomer repeat units constituting it, but has partially undergone, for example, radical decomposition or recombination due to radiation irradiation.

The cationic polymer may be composed only of at least one kind of constituent monomers selected from the group consisting of alkyleneimine, vinylamine, allylamine, lysine, protamine, and diallyldimethylammonium chloride. Alternatively, the cationic polymer may form a copolymer with one or more kinds of other monomers that do not adversely affect the antithrombogenicity. The other constituent monomers forming the copolymer are not limited, and examples of such monomers include constituent monomers B such as ethylene glycol, propylene glycol, vinylpyrrolidone, vinyl alcohol, vinylcaprolactam, vinyl acetate, styrene, methyl methacrylate, hydroxyethyl methacrylate, and siloxane. When the weight of the constituent monomers B is too high, the ionic bonding between the cationic polymer and the anionic sulfur compound having anticoagulant activity is weak. Therefore, the weight of the constituent monomers B with respect to the total weight of the cationic polymer is preferably not more than 10 wt %.

When the weight average molecular weight of the cationic polymer is too low, and lower than the molecular weight of the anionic sulfur compound having anticoagulant activity, stable ionic bonds cannot be formed so that the antithrombogenicity of interest is less likely to be obtained. On the other hand, when the weight average molecular weight of the cationic polymer is too high, the anionic sulfur compound having anticoagulant activity is included and embedded inside the cationic polymer. Thus, the weight average molecular weight of the cationic polymer is preferably 600 to 2,000,000, more preferably 1000 to 1,500,000, still more preferably 10,000 to 1,000,000. The weight average molecular weight of the cationic polymer can be measured by, for example, gel permeation chromatography or the light scattering method.

We discovered that, from the viewpoint of suppressing thrombus formation caused by the endovascular treatment aiding device, and allowing exertion of high antithrombogenicity continuously for a long period, there is a preferred value of the abundance ratio of sulfur atoms to the abundance of total atoms on the surface of the filter 6 as measured by X-ray photoelectron spectroscopy (hereinafter referred to as "XPS"). The abundance ratio of atoms is expressed as "atomic percent". The atomic percent means the abundance ratio of a particular kind of atoms to the abundance of total atoms, which is taken as 100, in terms of the number of atoms.

That is, the abundance ratio of sulfur atoms to the abundance of total atoms on the surface of the filter 6 as measured by XPS is preferably 3.0 to 6.0 atomic percent, more preferably 3.2 to 5.5 atomic percent, still more preferably 3.5 to 5.0 atomic percent. When the abundance ratio of sulfur atoms to the abundance of total atoms is less than 3.0 atomic percent, the binding amount of the anionic sulfur compound having anticoagulant activity is small, and therefore the antithrombogenicity of interest required to suppress the thrombus formation due to the endovascular treatment aiding device is less likely to be obtained. On the other hand, when the abundance ratio of sulfur atoms to the abundance of total atoms is higher than 6.0 atomic percent, the binding amount of the anionic sulfur compound having anticoagulant activity is sufficient, and the antithrombogenicity of interest can therefore be obtained, but the amount of the cationic polymer covalently bound to the filter 6 for allowing the ionic bonding needs to be large. Moreover, as elution of the anionic sulfur compound having anticoagulant activity proceeds, the exposed cationic polymer may exhibit hemolytic toxicity and/or the like, which is not preferred.

More specifically, the abundance ratio of sulfur atoms to the abundance of total atoms on the surface of the filter 6 as measured by XPS can be determined by XPS.

Measurement Conditions

Apparatus: ESCALAB 220iXL (manufactured by VG Scientific)

Excitation X-ray: monochromatic AlK α1, 2 ray (1486.6 eV)

X-ray diameter: 1 mm

X-electron escape angle: 90° (the angle of the detector with respect to the surface of the filter 6)

The surface of the filter 6 as measured by XPS herein means the portion from the measurement surface to a depth of 10 nm as detected under the measurement conditions in XPS wherein the X-electron escape angle, that is, the angle of the detector with respect to the surface constituted of the antithrombogenic compound and the filter 6, is 90°. The filter 6 may or may not contain sulfur atoms.

By radiating X-ray to the surface of the filter 6, and measuring the energy of photoelectrons generated therefrom, the binding energy values of bound electrons in the substance can be obtained. From the binding energy values, information on the atoms on the surface of the filter 6 as measured by XPS can be obtained, and, from the energy shift of the peak at each binding energy value, information on the valence and the binding state can be obtained. In addition, by using the area ratio of each peak, quantification, that is, calculation of the abundance ratios of various atoms, valences, and binding states, is possible.

More specifically, the S2p peak, which indicates the presence of sulfur atoms, appears near a binding energy value of 161 eV to 170 eV. We discovered that the area ratio of the S2p peak in the whole peak area is preferably 3.0 to 6.0 atomic percent. In the calculation of the abundance ratio of sulfur atoms to the abundance of total atoms, the obtained value is rounded to one decimal place.

Similarly, we discovered that there is a preferred value of the abundance ratio of nitrogen atoms to the abundance of total atoms on the surface of the filter 6 as measured by XPS. That is, the abundance ratio of nitrogen atoms to the abundance of total atoms on the surface of the filter 6 as measured by XPS is preferably 7.0 to 12.0 atomic percent, more preferably 7.5 to 11.0 atomic percent, still more preferably 8.0 to 10.0 atomic percent. When the abundance ratio of sulfur atoms to the abundance of total atoms is less than 7.0 atomic percent, the amount of the cationic polymer bound to the filter 6 is small so that the antithrombogenicity of interest required to suppress thrombus formation due to the endovascular treatment aiding device is less likely to be obtained. On the other hand, when the abundance ratio of nitrogen atoms to the abundance of total atoms is higher than 12.0 atomic percent, the amount of the cationic polymer bound to the filter 6 is large so that the anionic sulfur compound having anticoagulant activity bound to the cationic polymer by ionic bonding is present in a sufficient amount. However, we found that, as elution of the anionic sulfur compound having anticoagulant activity proceeds, a large amount of the cationic polymer is exposed to show hemolytic toxicity. More specifically, the N1s peak, which indicates the presence of nitrogen atoms, appears near a binding energy value of 396 eV to 403 eV. We discovered that the area ratio of the N1s peak in the whole peak area is preferably 7.0 to 12.0 atomic percent. The N1s peak can be split mainly into the n1 component (near 399 eV), which is attributed to carbon-nitrogen (hereinafter referred to as "C—N") bonds; and the n2 component (near 401 to 402 eV), which is attributed to ammonium salt, C—N(structure different from n1), and/or nitrogen oxide (hereinafter referred to as "NO"). The abundance ratio of each split peak component can be calculated according to Equation (1). In this calculation, the abundance ratio of nitrogen atoms to the abundance of total atoms, and the abundance ratio of each split peak component, are rounded to one decimal place.

$$\text{Split}_{ratio} = N1s_{ratio} \times (\text{Split}_{percent}/100) \qquad (1)$$

$\text{Split}_{ratio}$: abundance ratio of each split peak component (%)

$N1s_{ratio}$: abundance ratio of nitrogen atoms to the abundance of total atoms (%)

$\text{Split}_{percent}$: abundance ratio of each split peak component in the N1s peak (%)

The n2 component, which is attributed to NO, obtained by splitting the N1s peak indicates the presence of quaternary ammonium groups. We discovered that the abundance ratio of the n2 component in the total component of the N1s peak, that is, $\text{Split}_{percent}$ (n2), is preferably 20 to 70 atomic percent, more preferably 25 to 65 atomic percent, still more preferably 30 to 60 atomic percent. When $\text{Split}_{percent}$ (n2) is less than 20 atomic percent, the abundance of quaternary ammonium groups is low. Therefore, the ionic interaction with the anionic sulfur compound having anticoagulant activity is weak, and the elution rate is therefore high so that the antithrombogenicity of interest required to suppress thrombus formation due to the endovascular treatment aiding device is less likely to be obtained. On the other hand, when $\text{Split}_{percent}$ (n2) is higher than 70 atomic percent, the ionic interaction with the anionic sulfur compound having anticoagulant activity is too strong. In such cases, because of a decrease in the degree of freedom due to formation of ionic complexes, it is impossible to maintain a high anticoagulant activity for a long period, and the elution rate tends be low.

Because of the above reasons, the abundance ratio of the n2 component, that is, $Split_{ratio}$ (n2), which is calculated according to Equation (1), is preferably 1.4 to 8.4 atomic percent, more preferably 1.8 to 7.2 atomic percent, still more preferably 2.4 to 6.0 atomic percent.

The C1s peak, which indicates the presence of carbon atoms, appears near a binding energy value of 282 to 292 eV. The C1s peak can be split mainly into the c1 component (near 285 eV), which is attributed to carbon-hydrogen (hereinafter referred to as "CHx") bonds suggesting the presence of a saturated hydrocarbon(s) and/or the like, to carbon-carbon (hereinafter referred to as "C—C") bonds, and/or to carbon=carbon (hereinafter referred to as "C=C") bonds; the c2 component (near 286 eV), which is attributed to carbon-oxygen (hereinafter referred to as "C—O") bonds suggesting the presence of an ether(s) and/or hydroxyl groups, and/or to carbon-nitrogen (hereinafter referred to as "C—N") bonds; the c3 component (near 287 to 288 eV), which is attributed to carbon=oxygen (hereinafter referred to as "C=O") bonds suggesting the presence of carbonyl groups; the c4 component (near 288 to 289 eV), which is attributed to oxygen=carbon-oxygen (hereinafter referred to as "O=C—O") bonds suggesting the presence of ester groups and/or carboxyl groups; and the c5 component (near 290 to 292 eV), which is attributed to π-π* satellite peak (hereinafter referred to as "π-π") bonds suggesting the presence of a conjugated system(s) such as benzene rings. The abundance ratio of each split peak component can be calculated according to Equation (2). In this calculation, the abundance ratio of carbon atoms to the abundance of total atoms, and the abundance ratio of each split peak component, are rounded to one decimal place.

$$Split_{ratio} = C1s_{ratio} \times (Split_{percent}/100) \quad (2)$$

$Split_{ratio}$: abundance ratio of each split peak component (%)

$C1s_{ratio}$: abundance ratio of carbon atoms to the abundance of total atoms (%)

$Split_{percent}$: abundance ratio of each split peak component in the C1s peak (%)

The c3 component, which is attributed to C=O bonds, obtained by splitting the C1s peak indicates the presence of amide groups. We discovered that the abundance ratio of the c3 component in the total component of the C1s peak, that is, the abundance ratio of amide groups, is preferably not less than 2.0 atomic percent, more preferably not less than 3.0 atomic percent. When the abundance ratio of the amide groups is less than 2.0 atomic percent, the number of covalent bonds due to amide bonds between the cationic polymer and the filter 6 is small and, therefore, the binding amount of the cationic polymer is small. Moreover, since the state of ionic bonding between the cationic polymer and the anionic sulfur compound having anticoagulant activity is poor, the antithrombogenicity of interest is less likely to be obtained.

In addition, as another/other antithrombogenic material(s), an anionic polymer(s) containing, as constituent monomers, at least one compound selected from the group consisting of acrylic acid, methacrylic acid, α-glutamic acid, γ-glutamic acid, and aspartic acid; and/or at least one anionic compound selected from the group consisting of dicarboxylic acids such as oxalic acid, malonic acid, succinic acid, fumaric acid, glutaric acid, adipic acid, pimelic acid, suberic acid, azelaic acid, sebacic acid, malic acid, tartaric acid, and dodecanedioic acid, and citric acid;

is/are preferably bound to the filter 6 and/or the cationic polymer. The anionic polymer(s) and/or anionic compound(s) can be bound to the cationic polymer by ionic bonding.

The anionic polymer is preferably, but does not necessarily need to be, a polyacrylic acid (hereinafter referred to as "PAA"), polymethacrylic acid, poly(α-glutamic acid), poly (γ-glutamic acid), or polyaspartic acid since, when the weight ratio of anionic functional groups is high, the amount of the anionic polymer bound to the filter 6 can be large. The anionic polymer is more preferably a PAA.

Specific examples of the PAA include "polyacrylic acid" (manufactured by Wako Pure Chemical Industries, Ltd.). The PAA may be a copolymer with other monomers, or may be a modified body as long as the desired effect is not deteriorated.

From the viewpoint of safety and the like, elution of the anionic polymer into blood is not preferred. Thus, the anionic polymer is preferably bound, more preferably covalently bound, to the surface of the filter 6.

The anionic polymer may be either a homopolymer or a copolymer. When the anionic polymer is a copolymer, the copolymer may be any of a random copolymer, block copolymer, graft copolymer, and alternating copolymer.

The anionic polymer may be constituted only by the constituent monomers described above, or may form a copolymer with constituting monomers other than those described above as long as the antithrombogenicity is not adversely affected. The constituent monomers other than acrylic acid, methacrylic acid, α-glutamic acid, γ-glutamic acid, and aspartic acid to be used for forming the copolymer are not limited, and examples of such monomers include constituent monomers B such as ethylene glycol, propylene glycol, vinylpyrrolidone, vinyl alcohol, vinylcaprolactam, vinyl acetate, styrene, methyl methacrylate, hydroxyethyl methacrylate, and siloxane. When the weight of the constituent monomers B is too high, the number of reaction sites for binding to the filter 7 or to the other antithrombogenic compound(s) is small. Accordingly, the weight of the constituent monomers B with respect to the total weight of the anionic polymer is preferably not more than 10 wt %.

The anionic compound is preferably, but does not necessarily need to be, oxalic acid, malonic acid, succinic acid, fumaric acid, glutaric acid, adipic acid, pimelic acid, suberic acid, azelaic acid, sebacic acid, malic acid, tartaric acid, and/or citric acid since, when the weight ratio of anionic functional groups is high, a larger amount of the anionic compound can be bound to the filter 6 or the other antithrombogenic compound(s). The anionic compound is more preferably succinic acid.

When the weight average molecular weight of the anionic polymer is too small, the amount of the polymer bound to the filter 6 or to the other antithrombogenic compound(s) is small. It is therefore difficult to obtain a high and long-lasting antithrombogenicity. On the other hand, when the weight average molecular weight of the anionic polymer is too high, the antithrombogenic compound is included in the inside. Therefore, the weight average molecular weight of the anionic polymer is preferably 600 to 2,000,000, more preferably 10,000 to 1,000,000.

The surface amount of the anionic sulfur compound having anticoagulant activity on the filter 6 after soaking in physiological saline at 37° C. for 30 minutes was measured based on the anti-factor Xa activity. The anti-factor Xa activity herein is an index indicating the degree of inhibition of the activity of factor Xa, which promotes conversion of prothrombin to thrombin. By this, the surface amount of the compound can be known in terms of the unit of activity. For the measurement, "TEST TEAM (registered trademark) Heparin S" (manufactured by Sekisui Medical Co., Ltd.) (hereinafter referred to as TEST TEAM Heparin) was used. When the anti-factor Xa activity is too low, the surface amount of the anionic sulfur compound having anticoagulant activity on the filter 6 is small so that the antithrombogenicity of interest is less likely to be obtained. That is, the anti-factor Xa activity is preferably 30 mIU/cm$^2$, more preferably 50 mIU/cm$^2$. More specifically, the surface amount was measured as follows. The filter 6 to which the anionic sulfur compound having anticoagulant activity is bound was cut into a test piece having an effective surface area of about 0.26 cm$^2$, and the test piece was then soaked in 0.5 mL of physiological saline at 37° C. for 30 minutes. To the filter 6 after the soaking, 0.02 mL of human blood plasma, 0.02 mL of the antithrombin III liquid in TEST TEAM Heparin, and 0.16 mL of a buffer were added to provide a sample, and the sample was then allowed to react according to the operation procedure for TEST TEAM Heparin (end-point method). The absorbance at 405 nm was measured using a microplate reader (MTP-300, manufactured by Corona Electric Co., Ltd.). Using a calibration curve separately prepared using Heparin Sodium Injection (manufactured by Ajinomoto Pharmaceuticals Co., Ltd.), the surface amount was calculated. The heating time of the sample in the end-point method was 6 minutes.

The endovascular treatment aiding device is characterized in that, irrespective of the fact that the total binding amount of the anionic sulfur compound having anticoagulant activity on the filter 6 as measured based on the anti-factor Xa activity is small, the surface amount after soaking in physiological saline at 37° C. for 30 minutes is large. The total binding amount herein is the sum of the amount of the anionic sulfur compound having anticoagulant activity eluted in human blood plasma (product number, 12271210; manufactured by COSMO BIO Co., Ltd.) after 24 hours of soaking in the human blood plasma at 37° C., as calculated based on the anti-factor Xa activity, and the surface amount of the anionic sulfur compound having anticoagulant activity on the filter 6 after the 24 hours of soaking, as calculated based on the anti-factor Xa activity. More specifically, the amount of the anionic sulfur compound having anticoagulant activity eluted as calculated based on the anti-factor Xa activity was evaluated as follows. The filter 6 to which the anionic sulfur compound having anticoagulant activity is bound was cut into a test piece having an effective surface area of about 4.24 cm$^2$, and the test piece was then soaked in 1.5 mL of human blood plasma at 37° C. for 24 hours. To 0.04 mL of the resulting human blood plasma, 0.04 mL of the antithrombin III liquid in TEST TEAM Heparin and 0.32 mL of a buffer were added to provide a sample, and the sample was then allowed to react according to the operation procedure for TEST TEAM Heparin (end-point method). The absorbance at 405 nm was measured using a microplate reader. Using a calibration curve separately prepared using Heparin Sodium Injection, the amount of the anionic sulfur compound having anticoagulant activity eluted was calculated. The heating time of the sample in the end-point method was 5 minutes. The surface amount of the anionic sulfur compound having anticoagulant activity on the filter 6 after the 24 hours of soaking, as calculated based on the anti-factor Xa activity, was determined in the same manner as the surface amount of the anionic sulfur compound having anticoagulant activity on the filter 6 after soaking in physiological saline at 37° C. for 30 minutes as calculated based on the anti-factor Xa activity, except that the filter 6 after the 24 hours of soaking was used.

When the total binding amount is too large, the microstructure on the surface of the filter 6 is destroyed, while when the total binding amount is too small, the antithrombogenicity of interest is less likely to be obtained. That is, preferably, the total binding amount of the anionic sulfur compound having anticoagulant activity on the filter 6 as measured based on the anti-factor Xa activity is not more than 10,000 mIU/cm$^2$, and the surface amount of the anionic sulfur compound having anticoagulant activity on the filter 6 after soaking in physiological saline at 37° C. for 30 minutes as calculated based on the anti-factor Xa activity is not less than 30 mIU/cm$^2$. More preferably, the total binding amount is not more than 5000 mIU/cm$^2$, and the surface amount is not less than 50 mIU/cm$^2$.

The endovascular treatment aiding device is characterized in the elution behavior of the anionic sulfur compound having anticoagulant activity on the filter 6. That is, elution of the anionic sulfur compound having anticoagulant activity hardly occurs when the filter 6 is soaked in physiological saline at 37° C., while the elution rapidly occurs when the filter 6 is soaked in human blood plasma (product number, 12271210; manufactured by COSMO BIO Co., Ltd.) at 37° C. More specifically, during 1 hour of soaking in human blood plasma at 37° C., elution of not less than 50%, more preferably not less than 70%, still more preferably not less than 80%, of the total binding amount occurs. Similarly, during 15 minutes of soaking, elution of not less than 50%, more preferably not less than 70%, still more preferably not less than 80%, of the total binding amount occurs.

In terms of the range of the thickness of the antithrombogenic compound layer, when the layer is too thick, the microstructure on the surface of the filter 6 is destroyed and, moreover, thrombus formation may occur due to the change in the pore size and the change in the outer diameter of the opening-section side in the state where the filter section 3 is closed. That is, the thickness is preferably 1 to 600 nm.

The thickness of the antithrombogenic compound layer herein can be determined by, for example, combination of a scanning transmission electron microscope (hereinafter referred to as "STEM"), XPS, and/or the like. More specifically, when observation of the atomic distribution in the vertical direction from the interface of the filter 6 toward the inside is carried out, the thickness of the antithrombogenic compound layer means the distance from the start point to the end point of the range in which atoms derived from the antithrombogenic material layer are found. The thickness is measured as the mean of thickness values observed at at least three points.

The interface of the filter 6 as measured by STEM herein means the boundary between the acrylic resin or the like used for embedding the filter 6 in the sample preparation before the measurement by STEM, and the surface of the layer composed of the filter 6 and the antithrombogenic compound.

More specifically, STEM has detectors such as an energy dispersive X-ray spectrometer (hereinafter referred to as "EDX") and an electron energy-loss spectrometer (hereinafter referred to as "EELS"). Measurement conditions for the STEM are as follows.

Measurement Conditions

Apparatus: field emission transmission electron microscope JEM-2100F (manufactured by JEOL Ltd.)

EELS detector: GIF Tridiem (manufactured by GATAN, Inc.)

EDX detector: JED-2300T (manufactured by JEOL Ltd.)

Image acquisition: Digital Micrograph (manufactured by GATAN, Inc.)

Sample preparation: ultrathin sectioning (suspension using a copper microgrid; use of an acrylic resin as an embedding resin)
Acceleration voltage: 200 kV
Beam diameter: 0.7-nm diameter
Energy resolution: about 1.0 eV FWHM The presence of each kind of atoms is judged based on whether a peak intensity derived from the atoms can be found in a spectrum obtained by STEM measurement after subtraction of the background.

EXAMPLES

Examples of the endovascular treatment aiding device 1 are concretely described below with reference to figures. Our treatment aids are described below in detail by way of Examples and Comparative Examples. However, this disclosure is not limited thereto.

Example 1

An endovascular treatment aiding device 1 according to FIG. 1 was prepared. More specifically, the filter 6 was constituted of a mesh using monofilament polyester (PET) fibers having a fiber diameter of 28 µm such that the pore size was 100 µm on a side. This mesh was prepared such that the length in the longitudinal direction was about 10 mm, and the circular diameter of the filter opening section was 6 mm.

The coils 8 were prepared using a Pd—Re alloy wire having a wire diameter of 40 µm such that the outer diameter was 0.16 mm; the inner diameter was 0.08 mm; and the total length was 1 mm. The number of the coils 8 prepared was four. A NiTi alloy wire having a wire diameter of 42 µm was allowed to penetrate the coils. The four coils 8 were preliminarily wound around the NiTi alloy wire such that the coils were arranged at positions not including the peaks of the mountains and the peaks of the valleys in the state where the opening section of the filter section 3 was closed, and such that the circumference of the ring was equally divided into four segments by the positions where the coils 8 were arranged when the NiTi alloy wire was formed into a ring having an inner diameter of 6 mm. Fixation of the coils 8 was carried out using a polyurethane.

The NiTi alloy wire to which the four coils 8 were fixed was made into a ring shape by 5 times of winding such that the inner diameter was 6 mm, to provide a ring 7. The inner diameter portion of the ring 7 was fixed to the outer diameter portion of the opening section circle of the filter 6 using polyurethane.

As the supporting member 9, four aramid fibers having a fiber diameter of about 60 µm were used. The aramid fibers were bound to the filter 6, the ring 7, and the coils 8 such that each of the four aramid fibers was arranged at the midpoint of each coil 8, to prepare a filter section 3.

For the shaft 2, a stainless-steel wire having an outer diameter of 0.2 mm and a length in the longitudinal direction of 1800 mm was used. A taper shape was given to the wire such that the outer diameter of the portion from the distal end to a position about 20 mm distant therefrom in the longitudinal direction was 0.06 mm to 0.15 mm; the outer diameter of the shaft 2 in the next portion having a length of about 30 mm was 0.15 mm; and the outer diameter in the further next portion having a length of 20 mm was 0.15 mm to 0.2 mm, to prepare the shaft 2.

The shaft 2 was arranged such that it penetrated the closed-end section and the opening section of the filter section 3 and the polyimide tube bundling the supporting member 9, and such that the entire supporting member 9 had a uniform length, that is, such that the shaft 2 was positioned on the central axis of the ring 7. On the portion of the shaft 2 having an outer diameter of 0.15 mm, the supporting member 9 was fixed to the shaft 2 using a polyimide tube having an inner diameter of 0.25 mm, an outer diameter of 0.29 mm, and a length of 1.5 mm, using an adhesive.

The outer tube 4 was prepared such that it had a three-layer structure composed of a polytetrafluoroethylene inner layer, a braided layer of stainless-steel flat rectangular wires as an intermediate layer, and a polyimide outer layer, and had an inner diameter of 0.23 mm, an outer diameter of 0.36 mm, and a length of 1500 mm.

To the distal end of the outer tube 4, a polyimide tube having an inner diameter of 0.4 mm, an outer diameter of 0.52 mm, and a length of 5 mm was fixed using an adhesive such that a portion with a length of 4 mm protruded from the distal end, to provide an annular member 5.

The assembly composed of the outer tube 4 and the annular member 5 was arranged on the shaft 2 such that the annular member 5 was positioned in the distal side, to prepare the endovascular treatment aiding device 1.

Comparative Example 1

As Comparative Example 1, an endovascular treatment aiding device was prepared in the same manner except that the coils 8 were not used and, hence, that the coils 8 were not fixed to the ring 7.

Comparative Example 2

FILTERWIRE EZ (registered trademark), which is a thrombus capturing catheter manufactured by Boston Scientific Corporation having a constitution in which a supporting member is fixed to a shaft; the supporting member forms a ring in a filter section; a metal coil formed with a radio-opaque material is attached to an almost entire circumference of the ring; a sheet-shaped urethane filter on which a plurality of openings are formed is fixed to the ring; and the distal end of the filter is attached to the distal side of the shaft such that the filter is closed; was provided as Comparative Example 2. Comparative Example 2 was an endovascular treatment aiding device having a ring diameter of about 6 mm, a shaft length of 1900 mm, and a shaft diameter of 0.36 mm.

Comparative Example 3

As Comparative Example 3, an endovascular treatment aiding device was prepared in the same manner as in the Example except that the coils 8 were fixed to an almost entire circumference of the ring 7.

Comparative Experiment on Imaging Ability

A comparative experiment on the imaging ability was carried out for the Example, Comparative Example 1, Comparative Example 2, and Comparative Example 3, by an animal experiment using a pig with a body weight of 35 kg, using a radiation equipment OEC9800 Plus (GE Medical Systems). As a result, the filter section could be clearly observed in the Example, Comparative Example 2, and Comparative Example 3, but the filter section could not be found in Comparative Example 1.

Comparative Experiment on Particle Capture Rate

Figure 4:
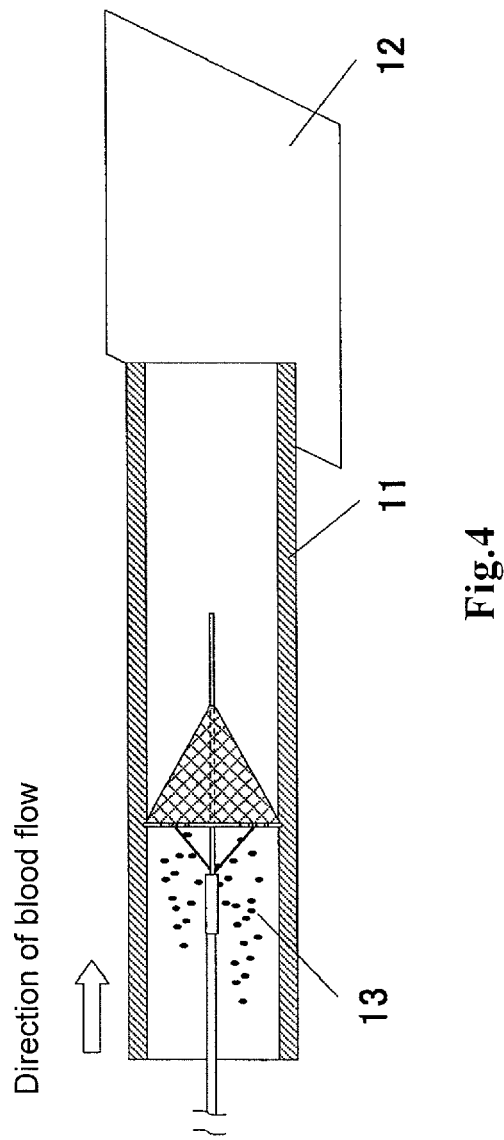
FIG. 4 is a schematic view showing an experimental model for comparison of the particle capture rate.

As shown in the schematic view showing an experimental model for comparison of the particle capture rate in FIG. 4, a tube 11 having an inner diameter of 5 mm was provided, and water was allowed to pass through the tube 11. Gauze 12 was provided at the distal end of the tube 11. The tube 11 was bent at an angle of about 45°, and, at the peak of the bent portion, the Example, Comparative Example 1, Comparative Example 2, or Comparative Example 3 contained in a delivery sheath was delivered to the site of placement of interest. Thereafter, the delivery sheath was removed to place the filter section in an expanded state in the tube 11, followed by allowing about 4000 particles 13 having a diameter of 150 μm to flow in the tube 11. Subsequently, an operation of retrieval of the endovascular treatment aiding device was carried out. An experiment was carried out for comparison of the particle capture rate based on the total number of particles that were allowed to flow, and the number of leaked particles. As a result, the Example and Comparative Example 1 showed particle capture rates of not less than 99%, while Comparative Example 2 and Comparative Example 3 showed particle capture rates of about 92% and about 88%, respectively.

Example 2

An endovascular treatment aiding device 1 according to FIG. 1 was prepared. More specifically, a mesh was prepared with monofilament polyester (PET) fibers having a fiber diameter of 28 μm such that the pore size was 100 μm on a side.

Subsequently, the mesh was soaked in an aqueous solution of 5.0 wt % potassium permanganate (manufactured by Wako Pure Chemical Industries, Ltd.) and 0.6 mol/L sulfuric acid (manufactured by Wako Pure Chemical Industries, Ltd.), and the reaction was allowed to proceed at 60° C. for 3 hours, thereby hydrolyzing and oxidizing the mesh (step of hydrolysis and oxidation). The aqueous solution after the reaction was removed, and the mesh was washed with hydrochloric acid (manufactured by Wako Pure Chemical Industries, Ltd.) and distilled water.

Subsequently, the mesh was soaked in an aqueous solution of 0.5 wt % 4-(4,6-dimethoxy-1,3,5-triazin-2-yl)-4-methylmorpholinium chloride n-hydrate (hereinafter referred to as "DMT-MM") (a condensing agent manufactured by Wako Pure Chemical Industries, Ltd.) and 5.0 wt % PEI (LUPASOL (registered trade mark) P, manufactured by BASF), followed by allowing the reaction to proceed at 30° C. for 2 hours, thereby covalently binding PEI to the mesh by condensation reaction (first coating step). The aqueous solution after the reaction was removed, and the mesh was washed with distilled water.

The mesh was further soaked in 1 wt % aqueous methanol solution of ethyl bromide (manufactured by Wako Pure Chemical Industries, Ltd.) or pentyl bromide (manufactured by Wako Pure Chemical Industries, Ltd.), and the reaction was allowed to proceed at 35° C. for 1 hour, and then at 50° C. for 4 hours, thereby allowing modification of PEI covalently bound to the surface of the mesh with quaternary ammonium (quaternary ammonium modification step). The aqueous solution after the reaction was removed, and the mesh was washed with methanol and distilled water.

Finally, the mesh was soaked in an aqueous solution (pH=4) of 0.75 wt % heparin sodium (manufactured by Organon API Inc.) and 0.1 mol/L sodium chloride, and the reaction was allowed to proceed at 70° C. for 6 hours, thereby allowing ionic bonding with PEI (second coating step). The aqueous solution after the reaction was removed, and the mesh was washed with distilled water.

A mesh treated with PEI (average molecular weight, about 600; manufactured by Wako Pure Chemical Industries, Ltd.) and ethyl bromide was provided as Mesh A; a mesh treated with PEI (LUPASOL (registered trade mark) P, manufactured by BASF), but not subjected to the quaternary ammonium modification step was provided as Mesh B; a mesh treated with PEI (LUPASOL (registered trade mark) P, manufactured by BASF) and ethyl bromide was provided as Mesh C; and a mesh treated with PEI (LUPASOL (registered trade mark) P, manufactured by BASF) and pentyl bromide was provided as Mesh D.

Using Meshes A to D, filters 6 having a length in the longitudinal direction of about 8 mm and a circular diameter of the opening-section side of 4 mm were prepared to provide Sample A, Sample B, Sample C, and Sample D, respectively. In Example 2, Samples A to D were used as filters 6.

The coils 8 were prepared using palladium-rhenium alloy wires having a wire diameter of 40 μm such that the outer diameter was 0.16 mm; the inner diameter was 0.08 mm; and the total length was 1 mm. The number of the coils 8 prepared was four. A nickel-titanium alloy wire having a wire diameter of 42 μm was allowed to penetrate the coils. The four coils 8 were preliminarily wound around the nickel-titanium alloy wire such that the coils 8 were arranged at positions not including the peaks of the mountains and the peaks of the valleys in the state where the opening section of the filter section 3 was closed, and such that the circumference of the ring 7 was equally divided into four segments by the positions where the coils 8 were arranged when the nickel-titanium alloy wire was formed into a ring 7 having an inner diameter of 6 mm. Fixation of the coils 8 was carried out using polyurethane.

The nickel-titanium alloy wire to which the four coils 8 were fixed was made into a ring shape by 5 times of winding such that the inner diameter was 6 mm, to provide a ring 7. The inner diameter portion of the ring 7 was fixed to the outer diameter portion of the opening section circle of the filter 6 using polyurethane.

As the supporting member 9, four polyarylate fibers having a fiber diameter of about 60 μm were used. The polyarylate fibers were bound to the filter 6, the ring 7, and the coils 8 such that the positional relationships shown in FIG. 3 were achieved by arranging each of the four polyarylate fibers at the midpoint of each coil 8, to prepare a filter section 3.

For the shaft 2, a stainless-steel wire having an outer diameter of 0.2 mm and a length in the longitudinal direction of 1800 mm was used. A taper shape was given to the wire such that the outer diameter of the portion from the distal end to a position about 20 mm distant therefrom in the longitudinal direction was 0.06 mm to 0.15 mm; the outer diameter of the shaft 2 in the next portion having a length of about 30 mm was 0.15 mm; and the outer diameter in the further next portion having a length of 20 mm was 0.15 mm to 0.2 mm, to prepare the shaft 2.

The shaft 2 was arranged such that it coaxially passed through the closed-end section and the opening section of the filter section 3 and the polyimide tube bundling the supporting member 9, and such that the entire supporting member 9 had a uniform length, that is, such that the shaft 2 was positioned on the central axis of the ring 7. On the portion of the shaft 2 having an outer diameter of 0.15 mm, the supporting member 9 was fixed to the shaft 2 using a polyimide tube having an inner diameter of 0.25 mm, an outer diameter of 0.29 mm, and a length of 1.5 mm, using an adhesive.

The outer tube 4 was prepared such that it had a three-layer structure composed of a polytetrafluoroethylene inner layer, a braided layer of stainless-steel flat rectangular wires as an intermediate layer, and a polyimide outer layer, and had an inner diameter of 0.23 mm, an outer diameter of 0.36 mm, and a length of 1500 mm.

To the distal end of the outer tube 4, a polyimide tube having an inner diameter of 0.4 mm, an outer diameter of 0.52 mm, and a length of 5 mm was fixed with an adhesive such that a portion with a length of 4 mm protruded from the distal end, to provide the annular member 5. To the distal end of the outer tube 4, a polyimide tube having an inner diameter of 0.4 mm, an outer diameter of 0.52 mm, and a length of 0.5 mm was fixed using an adhesive such that the end portions of the outer tube 4 and the polyimide tube joined together.

The annular member 5 had a total length of 2.5 mm and an inner diameter of 0.4 mm, and its outer diameter in the portion other than the thick section was 0.5 mm. The assembly composed of the outer tube 4 and the annular member 5 was arranged on the shaft 2 such that the annular member 5 was positioned in the distal side in the longitudinal direction, to prepare the endovascular treatment aiding device 1.

For the endovascular treatment aiding device 1 using Sample A as the filter 6, a comparative experiment on the imaging ability and a comparative experiment on the particle capture rate were carried out. The results are shown in Table 1. As shown in Table 1, the filter section could be clearly observed, and the particle capture rate was not less than 99%.

Samples A to D used for endovascular treatment aiding devices 1 were subjected to evaluation by the human whole blood test. The results are shown in Table 2. As shown in Table 2, no thrombus adhesion (−) was found for Sample A, and no thrombus adhesion (−−) was found for Samples B to D, in the evaluation by the human whole blood test.

Example 3

The first coating step was carried out by the same operation as in Mesh B in Example 2, and the mesh was then soaked in a solution of 0.5 wt % DMT-MM and 40 wt % succinic anhydride (manufactured by Wako Pure Chemical Industries, Ltd.) in dimethylacetamide, followed by allowing the reaction to proceed at 50° C. for 17 hours (first additional step). The solution after the reaction was removed, and the mesh was washed with methanol and distilled water.

The mesh was further immersed in an aqueous solution of 0.5 wt % DMT-MM and 5.0 wt % PEI, and the reaction was allowed to proceed at 30° C. for 2 hours (second additional step). The aqueous solution after the reaction was removed, and the mesh was washed with distilled water. The quaternary ammonium modification step using ethyl bromide was carried out by the same operation as in Mesh C in Example 2, and the second coating step was then carried out. The same reagents as in Example 2 were used except for the antithrombogenic compound.

A filter 6 prepared with a mesh subjected to the second additional step using PEI (LUPASOL (registered trade mark) P, manufactured by BASF) was provided as Sample E, and a filter 6 prepared with a mesh subjected to the second additional step using PEI (LUPASOL (registered trade mark) SK, manufactured by BASF) was provided as Sample F.

Samples E and F used for endovascular treatment aiding devices 1 were subjected to evaluation by the human whole blood test. The results are shown in Table 2. As shown in Table 2, no thrombus adhesion (−−) was found in the evaluation by the human whole blood test.

Example 4

The first coating step was carried out by the same operation as in Mesh B in Example 2, and the mesh was then soaked in an aqueous solution of 0.5 wt % DMT-MM and 0.5 wt % PAA (manufactured by Wako Pure Chemical Industries, Ltd.), followed by allowing the reaction to proceed at 30° C. for 2 hours (first additional step). The aqueous solution after the reaction was removed, and the mesh was washed with an aqueous sodium carbonate solution and distilled water.

The mesh was further soaked in an aqueous solution of 0.5 wt % DMT-MM and 5.0 wt % PEI, and the reaction was allowed to proceed at 30° C. for 2 hours (second additional step). The aqueous solution after the reaction was removed, and the mesh was washed with distilled water. The quaternary ammonium modification step using ethyl bromide was carried out by the same operation as in Mesh C in Example 2, and the second coating step was then carried out. The same reagents as in Example 2 were used except for the antithrombogenic compound.

A filter 6 prepared with a mesh subjected to the second additional step using PEI (average molecular weight, about 600; manufactured by Wako Pure Chemical Industries, Ltd.) was provided as Sample G; a filter 6 prepared with a mesh subjected to the second additional step using PEI (LUPASOL (registered trade mark) P, manufactured by BASF) was provided as Sample H; and a filter 6 prepared with a mesh subjected to the second additional step using poly(allylamine hydrochloride) (hereinafter referred to as "PAH") (weight average molecular weight, 900,000; manufactured by Sigma-Aldrich) was provided as Sample I.

Samples G to I used for endovascular treatment aiding devices 1 were subjected to evaluation by the human whole blood test. The results are shown in Table 2. As shown in Table 2, no thrombus adhesion (−−) was found in the evaluation by the human whole blood test.

Example 5

The first coating step was carried out by the same operation as in Example 2 except that PAH (weight average molecular weight, 900,000; manufactured by Sigma-Aldrich) or poly-L-lysine hydrobromide (hereinafter referred to as PLys) (average molecular weight, 30,000 to 70,000; manufactured by Sigma-Aldrich) was used instead of PEI. The quaternary ammonium modification step using ethyl bromide was carried out by the same operation as in Mesh C in Example 2, and the second coating step was then carried out. The same reagents as in Example 2 were used except for the antithrombogenic compound.

A filter 6 prepared with a mesh subjected to the first coating step using PAH instead of PEI was provided as Sample J, and a filter 6 prepared with a mesh subjected to the first coating step using PLys instead of PEI was provided as Sample K. The same reagents as in Example 2 were used except for the antithrombogenic compound.

Samples J and K used for endovascular treatment aiding devices 1 were subjected to evaluation by the human whole blood test. The results are shown in Table 2. As shown in Table 2, no thrombus adhesion (−) was found in the evaluation by the human whole blood test.

Example 6

A filter 6 prepared with a mesh subjected to the second coating step by the same operation as in Mesh C in Example 2 except that dextran sulfate sodium (Wako Pure Chemical Industries, Ltd.) was used instead of heparin sodium (manufactured by Organon API Inc.) was provided as Sample L. The same reagents as in Example 2 were used except for the antithrombogenic compound.

Sample L used for an endovascular treatment aiding device 1 was subjected to evaluation by the human whole blood test. The results are shown in Table 2. As shown in Table 2, no thrombus adhesion (−) was found in the evaluation by the human whole blood test.

Example 7

A mesh was soaked in an aqueous solution of 5% PEI, and irradiated with 5 kGy of γ-ray using a type JS-8500 Cobalt 60 γ-ray irradiator (manufactured by Nordion International Inc.) to allow covalent bonding (first coating step). The aqueous solution after the reaction was removed, and the mesh was washed with Triton-X100 (manufactured by Sigma-Aldrich), physiological saline, and distilled water. The quaternary ammonium modification step using ethyl bromide was carried out by the same operation as in Mesh C in Example 2, and the second coating step was then carried out. The same reagents as in Example 2 were used except for the antithrombogenic compound.

A filter 6 prepared with a mesh treated with PEI (average molecular weight, about 600; manufactured by Wako Pure Chemical Industries, Ltd.), but not subjected to the quaternary ammonium modification step, was provided as Sample M; a filter 6 prepared with a mesh treated with PEI (average molecular weight, about 600; manufactured by Wako Pure Chemical Industries, Ltd.) and ethyl bromide was provided as Sample N; a filter prepared with a mesh treated with (P; manufactured by BASF) and ethyl bromide was provided as Sample O; and a filter 6 prepared with a mesh treated with PEI (LUPASOL (registered trade mark) SK, manufactured by BASF) and ethyl bromide was provided as Sample P.

Samples M to P used for endovascular treatment aiding devices 1 were subjected to evaluation by the human whole blood test. The results are shown in Table 2. As shown in Table 2, no thrombus adhesion (−) was found for Samples M, N, and P, and no thrombus adhesion (−−) was found for Sample O, in the evaluation by the human whole blood test.

Example 8

A mesh was soaked in an aqueous solution of 5% PEI, and heated at 80° C. for 2 hours, thereby covalently binding PEI to the mesh by aminolysis reaction (first coating step). The aqueous solution after the reaction was removed, and the mesh was washed with distilled water. The quaternary ammonium modification step using ethyl bromide was carried out by the same operation as in Mesh C in Example 2, and the second coating step was then carried out. The same reagents as in Example 2 were used except for the antithrombogenic compound.

A filter 6 prepared with a mesh subjected to the first coating step using PEI (average molecular weight, about 600; manufactured by Wako Pure Chemical Industries, Ltd.) was provided as Sample Q; a filter 6 prepared with a mesh subjected to the first coating step using PEI (LUPASOL (registered trade mark) P, manufactured by BASF) was provided as Sample R; and a filter 6 prepared with a mesh subjected to the first coating step using PEI (LUPASOL (registered trade mark) SK, manufactured by BASF) was provided as Sample S.

Samples Q to S used for endovascular treatment aiding devices 1 were subjected to evaluation by the human whole blood test. The results are shown in Table 2. As shown in Table 2, no thrombus adhesion (−) was found in the evaluation by the human whole blood test.

Example 9

A filter 6 prepared with a mesh subjected to the first coating step using PEI (LUPASOL (registered trade mark) P, manufactured by BASF) and then to the quaternary ammonium modification step using ethyl bromide by the same operation as in Mesh C in Example 2, but not subjected to the second coating step, was provided as Sample T. The same reagents as in Example 2 were used except for the antithrombogenic compound.

Sample T used for an endovascular treatment aiding device 1 was subjected to evaluation by the human whole blood test. The results are shown in Table 2. As shown in Table 2, thrombus adhesion (+) was found in the evaluation by the human whole blood test.

Example 10

A filter 6 prepared with a mesh subjected to neither the first coating step using PEI nor the quaternary ammonium modification step, but subjected to the second coating step by the same operation as in Mesh C in Example 2, was provided as Sample U. The same reagents as in Example 2 were used except for the antithrombogenic compound.

Sample U used for an endovascular treatment aiding device 1 was subjected to evaluation by the human whole blood test. The results are shown in Table 2. As shown in Table 2, thrombus adhesion (+) was found in the evaluation by the human whole blood test.

Example 11

The first coating step was carried out by the same operation as in Example 2 except that polyvinyl pyrrolidone (hereinafter referred to as "PVP") (K-90, manufactured by ISP) was used instead of PEI. A filter 6 prepared with a mesh subjected to the quaternary ammonium modification step using ethyl bromide by the same operation as in Mesh C in Example 2 and then to the second coating step was provided as Sample V. The same reagents as in Example 2 were used except for the antithrombogenic compound.

Sample V used for an endovascular treatment aiding device 1 was subjected to evaluation by the human whole blood test. The results are shown in Table 2. As shown in Table 2, thrombus adhesion (+) was found in the evaluation by the human whole blood test.

Example 12

The first coating step was carried out by the same operation as in Example 2 except that benzalkonium chloride (manufactured by Wako Pure Chemical Industries, Ltd.) was used instead of PEI. A filter 6 prepared with a mesh subjected to the quaternary ammonium modification step using ethyl bromide by the same operation as in Mesh C in Example 2 and then to the second coating step was provided as Sample W. The same reagents as in Example 2 were used except for the antithrombogenic compound.

Sample W used for an endovascular treatment aiding device 1 was subjected to evaluation by the human whole blood test. The results are shown in Table 2. As shown in Table 2, thrombus adhesion (+) was found in the evaluation by the human whole blood test.

The endovascular treatment aiding devices were evaluated by the following methods for the antithrombogenicity, the imaging ability, and the particle capture ability.

Evaluation 1: Human Whole Blood Test

Filters 6 to which antithrombogenic compounds are bound (Samples A to W), and the same material as the untreated filter 6 (positive control), were cut into test pieces each having an effective surface area of 1.0 cm². The test pieces were soaked in physiological saline at 37° C. for 30 minutes, and then placed in 2-mL microtubes. After adding Heparin Sodium Injection (manufactured by Ajinomoto Pharmaceuticals Co., Ltd.) to fresh human blood to a concentration of 0.5 U/mL, 2 mL of the resulting human blood was added to each microtube, and the microtube was then incubated at 37° C. for 2 hours. Thereafter, the test piece was removed, and rinsed with PBS(−) (manufactured by Nissui Pharmaceutical Co., Ltd.), followed by quantifying the weight of thrombi attached. The thrombus weight was determined by measuring the dry weights of the test piece before the test and the test piece after the rinse, and calculating the difference between these weights. The test was carried out for each of Samples A to W and the positive control in three replicates. When the mean of the relative values of the thrombus weight measured in three replicates, calculated according to Equation (3), was not less than 20%, the sample was judged as having thrombus adhesion, and rated as (+). When the mean was less than 20% or less than 10%, the sample was judged as having no thrombus adhesion, and rated as (−) or (−−), respectively.

$$\text{Relative value of thrombus weight (\%)} = (Bt/Bp) \times 100 \quad (3)$$

Bt: thrombus weight on a filter 6 to which an antithrombogenic compound is bound Bp: thrombus weight of the positive control Evaluation 2: Comparative Experiment on Imaging Ability An experiment on the imaging ability was carried out for Example 2 by an animal experiment using a pig with a body weight of 35 kg, using a radiation equipment OEC9800 Plus (GE Medical Systems).

Evaluation 3: Comparative Experiment on Particle Capture Rate

As shown in the schematic view showing an experimental model for comparison of the particle capture rate in FIG. 4, a tube 11 having an inner diameter of 5 mm was provided, and water was allowed to pass through the tube 11. Gauze 12 was provided at the distal end of the tube 11. The tube 11 was bent at an angle of about 45°, and, at the peak of the bent portion, Example 2 contained in a delivery sheath was delivered to the site of placement of interest. Thereafter, the delivery sheath was removed to place the filter section in an expanded state in the tube 11, followed by allowing about 4000 particles 13 having a diameter of 150 μm to flow in the tube 11. Subsequently, an operation of retrieval of the endovascular treatment aiding device was carried out. An experiment was carried out for measurement of the particle capture rate based on the total number of particles that were allowed to flow, and the number of leaked particles. The results are shown in Table 1. Table 1 also shows the results of the Comparative Examples 1 to 3.

TABLE 1

| | | Members | | | Particle Capture |
| | Specification | Antithrombogenic compound | Coil | Imaging ability | Rate (%) |
| --- | --- | --- | --- | --- | --- |
| Example 2 | Antithrombogenic endovascular treatment aiding device 1 | Yes | Arranged at positions not containing peaks of mountains and peaks of valleys | Filter section could be clearly observed | Not less than 99% |
| Comparative Example 1 | Antithrombogenic endovascular treatment aiding device | Yes | No | Filter section could not be clearly observed | Not less than 99% |
| Comparative Example 2 | FilterWire EZ (registered trademark) | No | Arranged on almost entire circumference | Filter section could be clearly observed | 92% |
| Comparative Example 3 | Antithrombogenic endovascular treatment aiding device | Yes | Arranged on almost entire circumference | Filter section could be clearly observed | 88% |

TABLE 2

| | | Antithrombogenic compound | | | | | | |
| | Sample | Cationic polymer | Anionic sulfur compound having anticoagulant activity | Abundance ratio of sulfur atoms (atomic percent) | Abundance ratio of nitrogen atoms (atomic percent) | Surface amount based on anti-factor Xa activity (mIU/cm²) | Thickness of antithrombogenic compound layer (nm) | Carbon number of alkyl group | Thrombus adhesion |
| --- | --- | --- | --- | --- | --- | --- | --- | --- | --- |
| Example 2 | A | PEI | Heparin | 1.4 | 3.4 | 15.7 | 14 | 2 | − |
| | B | PEI | Heparin | 4.0 | 8.3 | 64.2 | 58 | 0 | − |
| | C | PEI | Heparin | 3.8 | 8.2 | 83.5 | 58 | 2 | − |
| | D | PEI | Heparin | 3.9 | 8.0 | 88.6 | 61 | 5 | − |

TABLE 2-continued

| | Sample | Cationic polymer | Anionic sulfur compound having anticoagulant activity | Abundance ratio of sulfur atoms (atomic percent) | Abundance ratio of nitrogen atoms (atomic percent) | Surface amount based on anti-factor Xa activity (mIU/cm$^2$) | Thickness of antithrombogenic compound layer (nm) | Carbon number of alkyl group | Thrombus adhesion |
|---|---|---|---|---|---|---|---|---|---|
| Example 3 | E | PEI | Heparin | 3.3 | 8.0 | Not less than 100 | 510 | 2 | − |
| | F | PEI | Heparin | 3.5 | 8.2 | Not less than 100 | 415 | 2 | − |
| Example 4 | G | PEI | Heparin | 4.3 | 8.9 | Not less than 100 | 395 | 2 | − |
| | H | PEI | Heparin | 3.9 | 9.8 | Not less than 100 | 585 | 2 | − |
| | I | PEI, PAH | Heparin | 3.4 | 6.5 | 55.4 | 368 | 2 | − |
| Example 5 | J | PAH | Heparin | 3.2 | 7.3 | 52.3 | 10 | 2 | − |
| | K | PLys | Heparin | 3.2 | 7.1 | 41.5 | 12 | 2 | − |
| Example 6 | L | PEI | Dextran sulfate | 3.6 | 8.2 | — | 60 | 2 | − |
| Example 7 | M | PEI | Heparin | 1.0 | 2.5 | 3.2 | 6 | 0 | − |
| | N | PEI | Heparin | 1.0 | 2.4 | 8.2 | 6 | 2 | − |
| | O | PEI | Heparin | 3.1 | 6.4 | 25.5 | 20 | 2 | − |
| | P | PEI | Heparin | 1.0 | 2.9 | 8.4 | 11 | 2 | − |
| Example 8 | Q | PEI | Heparin | 1.1 | 2.6 | 8.8 | 9 | 2 | − |
| | R | PEI | Heparin | 1.1 | 3.4 | 10.5 | 10 | 2 | − |
| | S | PEI | Heparin | 1.1 | 3.1 | 10.1 | 10 | 2 | − |
| Example 9 | T | PEI | — | 0.3 | 8.1 | — | 49 | 2 | + |
| Example 10 | U | — | Heparin | 0.8 | — | 0 | <1 | — | + |
| Example 11 | V | PVP | Heparin | 1.2 | 2.5 | 0.5 | 10 | 2 | + |
| Example 12 | W | Benzalkonium chloride | Heparin | 1.5 | 2.9 | 2.3 | 10 | 2 | + |

INDUSTRIAL APPLICABILITY

Our treatment aids can be used as an endovascular treatment aiding device when an endovascular treatment such as balloon angioplasty or stenting using a balloon catheter or a stent is carried out.

The invention claimed is:

1. An endovascular treatment aiding device comprising:
a flexible shaft;
a filter fixed to said shaft such that a closed-end section is formed in a distal side in a longitudinal direction of the shaft, and an opening section is formed in a proximal side in said longitudinal direction, wherein a ring having elastic restoring force is fixed to said opening section, which filter is in a conical shape having a bottom formed by said ring when said filter is open, and can be opened and closed in an umbrella-like manner; and
a supporting member composed of linear members each of which is fixed to said ring and a part of said shaft such that they are connected to each other, which linear members enable closing said filter by tension caused by application of an external force to the proximal side in said longitudinal direction;
wherein
coils formed with a radio-opaque material are wound around said ring;
when said filter is closed, a plurality of mountains pointing toward the distal side in said longitudinal direction and a plurality of valleys pointing toward the proximal side in said longitudinal direction are alternately formed in said ring to form a shape in which said mountains are positioned close to each other, and said valleys are positioned close to each other;
said coils are arranged on said ring such that said coils contain positions fixed by said supporting member on said ring, but do not contain positions of the peaks of said mountains and the peaks of said valleys; and
a ratio of abundance of sulfur atoms to abundance of total atoms on the surface of said filter as measured by X-ray photoelectron spectroscopy (XPS) is 3.0 to 6.0 atomic percent.

2. The endovascular treatment aiding device according to claim 1, wherein the opening section of said filter and said ring are fixed to each other through an elastomer material.

3. The endovascular treatment aiding device according to claim 1, wherein said coils and said ring are fixed to each other through an elastomer material.

4. The endovascular treatment aiding device according to claim 1, wherein a cationic polymer containing as a constituent monomer at least one compound selected from the group consisting of alkyleneimine, vinylamine, allylamine, lysine, protamine, and diallyldimethylammonium chloride is covalently bound to said filter, and an anionic sulfur compound having anticoagulant activity is bound to said filter and/or said cationic polymer.

5. The endovascular treatment aiding device according to claim 4, wherein said anionic sulfur compound having anticoagulant activity is at least one selected from the group consisting of heparin and heparin derivatives.

6. The endovascular treatment aiding device according to claim 4, wherein a surface amount of said anionic sulfur compound having anticoagulant activity on said filter after soaking in physiological saline at 37° C. for 30 minutes as measured based on anti-factor Xa activity is not less than 30 mIU/cm$^2$.

7. The endovascular treatment aiding device according to claim 4, wherein said cationic polymer and said anionic sulfur compound having anticoagulant activity form an antithrombogenic compound layer with a thickness of 1 to 600 nm on a surface of said filter.

8. The endovascular treatment aiding device according to claim 1, wherein a ratio of abundance of nitrogen atoms to abundance of total atoms on the surface of said filter as measured by X-ray photoelectron spectroscopy (XPS) is 7.0 to 12.0 atomic percent.

9. The endovascular treatment aiding device according to claim 1, wherein said filter is formed with polyester.

* * * * *